United States Patent [19]

Sittig

[11] 4,130,365

[45] Dec. 19, 1978

[54] MASS TRANSFER IN LIQUID MEDIA

[75] Inventor: Wolfgang Sittig, Hofheim, Fed. Rep. of Germany

[73] Assignee: Hoechst Aktiengesellschaft, Frankfurt am Main, Fed. Rep. of Germany

[21] Appl. No.: 772,574

[22] Filed: Feb. 28, 1977

[30] Foreign Application Priority Data

Mar. 2, 1976 [DE] Fed. Rep. of Germany ....... 2608480

[51] Int. Cl.$^2$ .............................................. B01F 5/10
[52] U.S. Cl. .................................... 366/137; 422/235
[58] Field of Search ................ 259/4 R, 95, DIG. 17; 302/14, 66; 526/63, 88; 23/285; 48/210; 366/131, 136, 137, 159

[56] References Cited

U.S. PATENT DOCUMENTS

| | | | |
|---|---|---|---|
| 2,479,360 | 8/1949 | Howard | 526/63 |
| 2,856,272 | 10/1958 | Baeyaert | 526/63 |
| 3,034,859 | 5/1962 | Gunn | 23/285 |
| 3,297,657 | 1/1967 | Gray | 526/63 |

*Primary Examiner*—Robert W. Jenkins
*Attorney, Agent, or Firm*—Curtis, Morris & Safford

[57] ABSTRACT

In the case of reactions in the liquid phase the reactants should be contacted with one another as intimately as possible. The economy of a process depends on the transfer of the reactants to the place were the reaction takes place and the removal of the reaction product. The mass transfer in liquid media can be improved by adding to the liquid medium 0.1 to 10% by volume of inert solid particles having a specific gravity which is by 1.1 to 20 times greater than that of the liquid medium and imparting to the liquid medium a movement such that the solid particles having a diameter of from 0.1 to 40 mm are kept in suspension.

5 Claims, 1 Drawing Figure

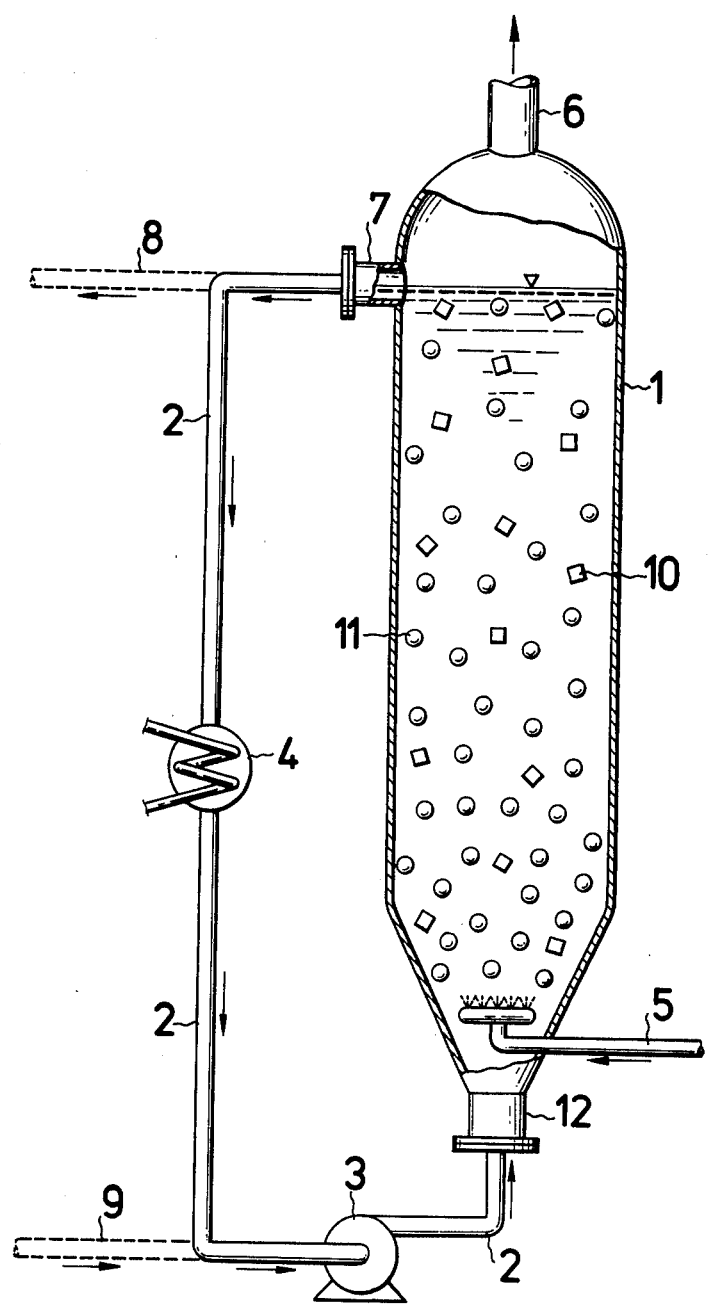

MASS TRANSFER IN LIQUID MEDIA

This invention relates to a process for improving the transport of substances in liquid media, for example gassed liquids, suspensions, emulsions and/or dispersions, especially in fermentation liquors.

When reactions are to be carried out in the liquid phase the necessary reactants must be transported by mixing and/or stirring to the place were the reaction takes place and the reaction product must be removed. When gaseous reactants are concerned the gas must be introduced into the liquid phase and transferred to the place of reaction through the gas-liquid interface. In the case of catalytic reactions, the paths of transfer are determined by the distribution of the catalytically substances, or in fermentations by the distribution of the cells.

It is known to carry out reactions of the afore-said types in vessels with stirrer, reactors with circulation, bubble columns or free jet reactors. In the case of high conversions, the power required to achieve the high transfer speed amounts to 5 kilowatts and more for one cubic meter of liquid. Accordingly, large amounts of additional thermal energy obtained have to be eliminated. Suspended catalysts or microorganisms having microscopical particle sizes do not permit diverging movements. In reactors provided with stirring means only parts of the volume of the liquid reaction mixture are agitated by the stirrer and consequently relatively low mass transfer rates are obtained. To ensure a high rate of mass transfer an intense mixing of very small areas of a reactor is, however, necessary. In vessels with stirrer and introduction of gas higher speeds of rotation result in demixing effects due to the occurring centrifugal forces.

There have also been proposed so-called fluidized bed processes with higher density of solid matter and processes in which microorganisms grow on particles. The fluidized bed process has the drawback that a large portion of the reaction space is blocked by the solid matter. In the case of microorganisms growing on particles, an additional separation process is required and there can only be used such microoganisms which have a sufficient adherence to the surface of the solid particles.

It is an object of the invention to provide a process making possible the mass transfer in liquid media with a minimum expenditure of energy and better distribution of the introduced energy.

It is proposed a process to improve the transfer of mass in liquid media with the use of inert solid particles having a higher specific gravity than the liquid medium, which comprises adding the solid particles to the liquid medium in an amount of from 0.1 to 10% by volume and keeping the medium in such a motion that the solid particles are suspended therein.

It proved especially advantageous to impart to the liquid medium a loop shape movement, for example to circulate the medium by pumping, to use solid particles the specific gravity of which is from 1.1 to 20 times greater than that of the liquid medium and to limit the average particle diameter to 0.1 to 40 mm.

To ensure a high rate of mass transfer an intense mixing in smallest areas of a reactor is necessary. The addition of solid particles having an average diameter of from 0.1 to 40 mm and a density which is by 1.1 to 20 times higher than that of the liquid medium produces a differential speed superposed upon the macroscopic movement of flow, which differential speed causes an inner mixing of the whole volume. To obtain the required mass transfer the solid matter is added in an amount corresponding to 0.1 to 10% by volume of the reactor content. The shape of the reactor is immaterial with the use of solid particles as long as areas with minor flow are avoided near the bottom.

The process of the invention will now be described in further detail and by way of example only with reference to the drawing which represents a sectional elevation of a reactor with the necessary equipement.

Referring to the drawing, the cylindrical or conical reactor (1) is charged with the liquid medium which is circulated by a circulating pump (3) through conduit (2). The liquid medium leaves the reactor (1) at (7) and re-enters it at (12). Oxygen-containing gas is introduced into the reactor (1) through conduit (5). The solid matter is fed to the reactor through short conduit (6) for the exhaust air. In the FIGURE the solid is represented by squares (10) and the process gas by circles (11). The solid particles (10) are kept in suspension by the movement of the liquid medium and between each solid particle and the liquid medium a field of differential velocity if formed which has a very advantageous effect on the mixing of the liquid medium. Gas bubbles ascending in the liquid medium and hitting the suspended solid particles are stimulated to internal convection and in the velocity field formed around the solid particles the interface between the gas and the liquid is renewed continuously. Both effects cause a lasting improvement of the mass transfer gaseous-liquid and, in the case of fermentation, from the liquid to the cells. In front of the overflow (7) a separating device for the solid particles (not shown) can be mounted. To eliminate the process heat a heat exchanger (4) can be inserted in conduit (2). In the case of continuous operation a partial current is removed from the reaction cycle through conduit (8) and a corresponding amount of fresh liquid medium is introduced through conduit (9).

The following examples illustrate the invention.

EXAMPLE 1

To produce Candida Lipolytica (ATCC 20383) 2,000 liters of a nutrient medium containing a n-paraffin, for example a $C_{14}$ to $C_{18}$ alkane fraction, $NH_3$, phosphates and other salts were introduced, together with 20 kilograms of polyethylene terephthalate having a particle size of about 3mm, into a fermentor having a diameter of 1 meter and a height of 2.5 meters and the mixture was circulated by pumping through a conduit having an internal diameter of 100 mm. The pumping energy was 0.8 kilowatt per cubic meter, corresponding to a circulated volume of 140 cubic meters per hour. Into the fermentor there were also introduced per hour 72 cubic meters of air of 1 bar.

After a fermentation period of 36 hours, the nutrient medium contained 27 grams of dry matter per liter, meaning that the content of Candida Lipolytica had been doubled within 4 hours.

In a fermentor of similar dimensions (diameter 1.2 m, height 2.5 m) a mechanical driving power of 7.8 kilowatts per cubic meter was required under otherwise identical conditions to produce 27 grams of dry matter per liter of liquid medium.

EXAMPLE 2

To enrich the oxygen content of water 2,000 liters of oxygen-free water were pumped through a reactor as described in Example 1 and gassed per hour with 120 Nm$^3$ (N meaning under normal conditions of pressure and temperature) of air of 1.2 bar. Without the addition of solid matter a volumetric oxygen transition coefficient $K_1 \cdot a$ of 320 h$^{-1}$ was obtained.

In the presence of 20 kilograms of polyethylene terephthalate having a particle diameter of about 3 mm the coefficient was $K_1 \cdot a = 400$ h$^{-1}$ under otherwise identical conditions.

What is claimed is:

1. In a process for transferring mass in liquid media with the aid of inert solid particles having a higher specific gravity than the liquid medium, the improvement which comprises the steps of adding solid particles to the liquid medium in an amount of from 0.1 to 10% by volume and maintaining said solid particles in suspension in the liquid medium throughout substantially the entire volume thereof by imparting to the liquid medium a substantially continuous movement by circulating the liquid medium in a loop shaped flow path.

2. The process of claim 1, wherein the solid particles have a specific gravitiy which is by 1.1 to 20 times higher than that of the liquid medium and the said particles have an average particle diameter of from 0.1 to 40 mm.

3. The process of claim 1 wherein said liquid medium is contained in a reactor vessel and said step of imparting movement to the liquid medium comprises continuously flowing a quantity of said liquid medium into the bottom of said reactor vessel in an upward direction.

4. The process of claim 3 further including the step of removing liquid medium from the reactor near the top thereof and circulating at least a portion of the removed liquid medium back to the bottom of the reactor for use in said flowing step.

5. In a process for tansferring mass in liquid media with the aid of inert solid particles having a higher specific gravity than the liquid medium, the improvement which comprises the steps of adding solid particles in the liquid medium in an amount of from 0.1 to 10% by volume and maintaining said solid particles in suspension in the liquid medium throughout substantially the entire volume thereof by imparting to the liquid medium in a substantially continuous movement; said liquid medium being contained in a reactor vessel and said step of imparting movement to the liquid medium comprising continuously flowing a quantity of liquid medium in the bottom of said reactor vessel in an upward direction.

* * * * *